United States Patent [19]

Nakatsu et al.

[11] Patent Number: 5,753,609
[45] Date of Patent: May 19, 1998

[54] FRAGRANCE COMPOSITION CONTAINING 4-(1-MENTHOXYMETHYL)-2-PHENYL-1,3-DIOXOLANE OR ITS DERIVATIVES

[75] Inventors: Tetsuo Nakatsu; Carter B. Green; Gary A. Reitz; Raphael K. L. Kang, all of Rockleigh, N.J.

[73] Assignees: Takasago International Corporation, Tokyo, Japan; Takasago Institute for Interdisciplinary Science, Inc., Rockleigh, N.J.

[21] Appl. No.: 642,886

[22] Filed: May 6, 1996

Related U.S. Application Data

[63] Continuation-in-part of Ser. No. 321,976, Oct. 12, 1994, Pat. No. 5,545,424.

[51] Int. Cl.$^6$ .................................................. A61K 7/46
[52] U.S. Cl. .................... 512/8; 512/1; 512/20; 512/25; 568/626
[58] Field of Search .................. 426/534, 536, 426/538, 650; 568/626, 664, 665, 666, 667; 512/1, 8, 14, 19, 20, 22, 23, 25

[56] References Cited

U.S. PATENT DOCUMENTS 4,459,425  7/1984  Amano et al. .

FOREIGN PATENT DOCUMENTS 57-188537  11/1982  Japan .
WO9210107  6/1992  WIPO .
WO9406441  3/1994  WIPO .

*Primary Examiner*—Leslie Wong
*Attorney, Agent, or Firm*—Sughrue, Mion, Zinn, Macpeak & Seas, PLLC

[57] ABSTRACT

4-(1-methoxymethyl)-2-phenyl-1,3-dioxolane or a derivative thereof represented by formula (I):

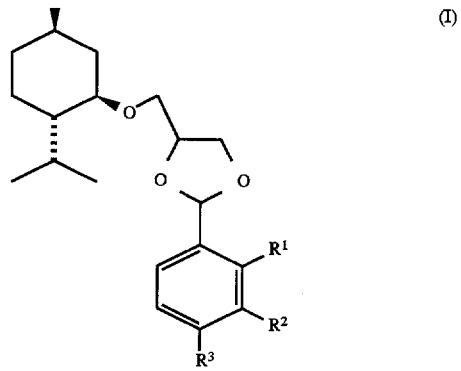

wherein $R^1$ represents a hydrogen atom, a hydroxy group or a lower alkoxy group; $R^2$ and $R^3$, which may be the same or different, each represents a hydrogen atom, a hydroxy group, a lower alkoxy group, or, when taken together, $R^2$ and $R^3$ represent a methylene dioxy group; useful in flavor and fragrance compositions.

7 Claims, No Drawings

FRAGRANCE COMPOSITION CONTAINING 4-(1-MENTHOXYMETHYL)-2-PHENYL-1,3-DIOXOLANE OR ITS DERIVATIVES

This application is a continuation-in-part application of and claims priority for U.S. Ser. No. 08/321,976, filed Oct. 12, 1994, now U.S. Pat. No. 5,545,424.

FIELD OF THE INVENTION

This invention relates to 4-(1-menthoxymethyl)-2-phenyl-1,3-dioxolane or its derivatives which are useful as an active ingredient for flavor or fragrance compositions.

BACKGROUND OF THE INVENTION

Various types of products incorporate ingredients which impart some kind of sensation to the mouth, oral cavity, throat or skin as a flavor or fragrance. Such products include toothpastes, mouthwashes, chewing gums, tobacco products, beverages and pharmaceutical products.

For example, 1-menthol and 3-(1-menthoxy)propane-1,2-diol are used as active ingredients in the products described above (e.g., as disclosed in U.S. Pat. No. 4,459,425). These products impart a cooling sensation to the mouth or skin.

PCT published application WO 92/10107 discloses that compound (II) represented by the following general formula:

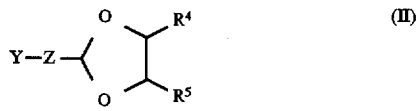

wherein $R^4$ and $R^5$ are independently —COOR$^6$ wherein $R^6$ is H or lower alkyl, provided that in at least one of $R^4$ and $R^5$, $R^6$ is lower alkyl; wherein Z is a direct bond, or —CH=C(R$^7$)—; where $R^7$ is H or an alkyl group; and Y is a group of the formula (III) or (IV):

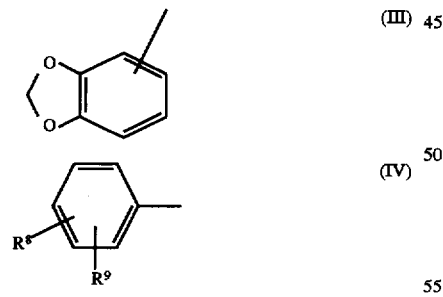

where $R^8$ and $R^9$ are independently H, lower alkyl or —OR$^{10}$ where $R^{10}$ is H or lower alkyl; is useful as a flavor.

However, an ingredient which can impart a more significant and/or stimulating sensation is desired for the consumer market. Moreover, such an ingredient must have good quality and have a long-lasting taste, odor or combination thereof.

On the other hand, it has been disclosed that a substituted benzaldehyde acetal compound represented by general formula (V):

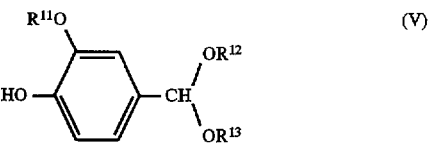

wherein $R^{11}$ is $C_{1-2}$ alkyl, $R^{12}$ and $R^{13}$ are each lower alkyl or $R^{12}$ and $R^{13}$, together with oxygen atom to which they bond may form, a cyclic group of the formula —O—R$^{14}$—O— where $R^{14}$ is a lower alkylene or alkylalkylene which may be substituted with a lower alkyl or OH;

is useful as a flavor and a fragrance (as disclosed in JP-A-57-188537 and WO 94/06441) (The term "JP-A" as used herein means an "unexamined published Japanese patent application").

However, those compounds do not impart a stimulating sensation or a long-lasting sensation to the mouth or skin.

SUMMARY OF THE INVENTION

Accordingly, an object of this invention is to provide a new flavor and fragrance compound while meeting the above-described requirements.

In view of the above, extensive investigations have been conducted and, as a result, this invention provides 4-(1-menthoxymethyl)-2-phenyl-1,3-dioxolane or its derivatives with enhanced taste and odor and thus a long-lasting taste and odor is achieved.

The present invention provides 4-(1-menthoxymethyl)-2-phenyl-1,3-dioxolane or a derivative thereof represented by formula (I):

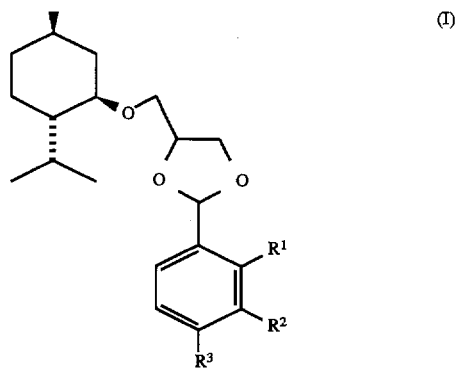

wherein $R^1$ represents a hydrogen atom, a hydroxy group or a lower alkoxy group, $R^2$ and $R^3$, which may be the same or different, each represents a hydrogen atom, a hydroxy group, a lower alkoxy group, or when taken together, $R^2$ and $R^3$ represent a methylene dioxy group.

The present invention further provides a flavor or fragrance composition containing the compound of formula (I) or a derivative thereof as an active ingredient.

DETAILED DESCRIPTION OF THE INVENTION

In formula (I), the lower alkoxy group as represented by $R^1$, $R^2$ and $R^3$ preferably contains from 1 to 4 carbon atoms, and specific examples thereof include a methoxy group, an ethoxy group, an n-propoxy group, an isopropoxy group, an n-butyloxy group and an isobutyloxy group.

More preferably, specific examples include a methoxy group and an ethoxy group.

Furthermore, specific examples of the preferred compound of the present invention represented by the formula (I), are compounds shown in Table 1 below, but the compounds of the formula (I) are not limited to these exemplified compounds.

In addition, in Table 1, Me, Et, Pr, and n-Bu represents a methyl group, an ethyl group, a propyl group, and an n-butyl group respectively.

TABLE 1

| Compound | R¹ | R² | R³ | Name |
|---|---|---|---|---|
| 1 | H | H | H | 4-(1-menthoxy-methyl)-2-phenyl-1,3-dioxolane-(Genzaldehyde-MPD) |
| 2 | H | OH | OH | 4-(1-menthoxy-methyl)-2-(3',4'-dihydroxyphenyl)-1,3-dioxolane (protocatechuic aldehyde-MPD) |
| 3 | H | OMe | OH | 4-(1-menthoxy-methyl)-2-(3'-methoxy-4'-hydroxyphenyl)-1,3-dioxolane(vanillin-MPD) |
| 4 | H | OEt | OH | 4-(1-menthoxy-methyl)-2-(3'-ethoxy-4'-hydroxyphenyl)-1,3-dioxolane(ethyl vanillin-MPD) |
| 5 | OH | OMe | H | 4-(1-menthoxy-methyl)-2-(2'-hydroxy-3'-methoxy-phenyl)-1,3-dioxolane(ortho vanillin-MPD) |
| 6 | H | H | OMe | 4-(1-menthoxy-methyl)-2-(4'-methoxyphenyl)-1,3-dioxolane (anisaldehyde-MPD) |
| 7 | H | —O—CH₂ | —O— | 4-(1-menthoxy-methyl)-2-(3',4'-methylenedioxyphenyl)-1,3-dioxolane(piperonal-MPD) |

The abbreviations in Table 1 above are described below:

MPD represents an acetal of 3-(1-menthoxy)propanediol.

Of these compounds, preferred examples include Compound 2 and Compound 3.

4-(1-Menthoxymethyl)-2-phenyl-1,3-dioxolane or derivatives of formula (I) can be produced, for example, using the following Reaction Scheme.

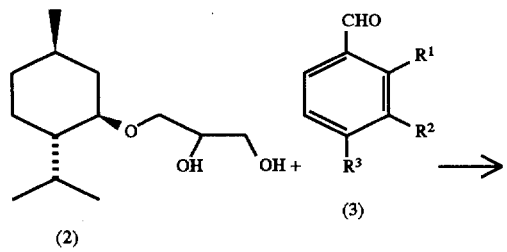

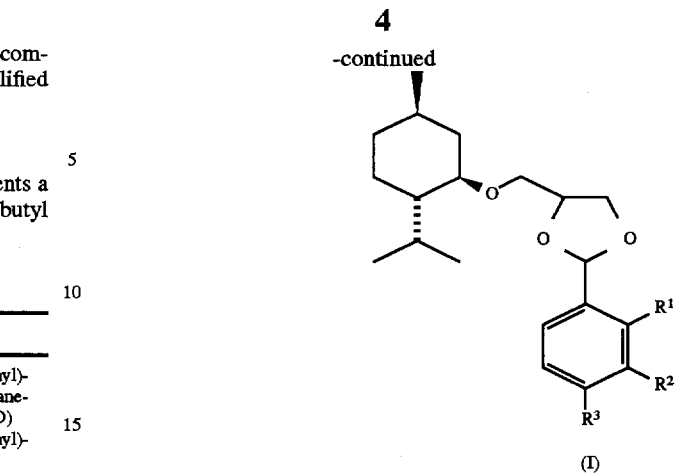

That is, 4-(1-menthoxymethyl)-2-phenyl-1,3-dioxolane or its derivatives of formula (I) can be easily synthesized by reaction of 3-(1-menthoxypropane-1,2-diol (2) with a benzaldehyde derivative (3) in the presence of an acid as a catalyst.

Examples of suitable benzaldehyde derivatives (3) include vanillin, protocatechuic aldehyde, ethyl-vanillin, ortho-vanillin, benzaldehyde, anisaldehyde and piperonal (heliotropin).

Suitable acids useful as a catalyst include any acid which is typically used in acetalization. Examples of suitable acids include hydrochloric acid, phosphoric acid, sulfuric acid, p-toluene sulfonic acid, acetic acid, anhydrous acetic acid, and propionic acid.

The reaction can be conducted in a similar manner to conventional acetalization chemistry.

It was found that the 4-(1-menthoxymethyl)-2-phenyl-1,3-dioxolane or its derivatives (I) obtained enhance taste or odor with a long-lasting taste and odor being produced.

Furthermore, it surprisingly turned out that the taste given off by the thus obtained 4-(1-menthoxymethyl)-2-phenyl-1,3-dioxolane or its derivatives (I) provides new and unexpected flavor characteristics.

For example, 4-(1-menthoxymethyl)-2-phenyl-1,3-dioxolane (Compound 3, vanillin-MPD) of the present invention has a hot, burning and tingling taste with a long-lasting taste.

Compound 3 is derived from vanillin and 3-(1-menthoxy)-1,2-propanediol. Vanillin is a common flavor or fragrance ingredient which is very sweet and has a strong vanilla-like odor. 3-(1-Menthoxy)-1,2-propanediol (produced by TAKASAGO INTERNATIONAL CORPORATION, U.S. Pat. No. 4,459,425) is also a flavor or fragrance ingredient which has a menthol-like taste and a cooling effect.

That is, the character of Compound 3 of the present invention is different from that of those prior art compounds described above.

Compound (I) of the present invention can be used to prolong other sensations such as cooling sensations, for example, in combination with 1-menthol, 3-(1-menthoxy)-1,2-propanediol or isopulegol. When cooling and longer lasting tingling sensations are added together, the result would signal prolonged cooling effects to the user.

The burning tingling or bitter sensations are desirable as signals to convey to the user a desired psychological or physiological effect.

Compound (I) of the present invention can be used in confectionery, beverages and other foods. More specifically, it can be used in chewing gums, candies, ice creams, ice candies, chocolates, snacks, cookies, cakes, breads, tea, coffee, juice, fruit wine, dairy drinks, carbonated drinks, etc.

Also, Compound (I) of the present invention can be used in cosmetic and pharmaceutical products. More specifically, it can be used in mouthwashes, toothpastes, antiperspirant products, deodorant products, colognes, perfumes, lip sticks, soaps, shampoos, hair rinses and detergents, etc.

A suitable amount of 4-(1-menthoxymethyl)-2-phenyl-1,3-dioxolane or its derivatives (I) according to the present invention which is used in a flavor composition or in a fragrance composition to be used in various products, wherein the amount used is from 0.0001 to 30% by weight, preferably from 0.0001 to 10% by weight and more preferably from 0.001 to 0.01% by weight, based on the total weight of the composition.

Although many novel synthesized molecules have various effects on the skin, they are often toxic and cannot be applied every day. In contrast, the present invention produces novel compounds that are safe for human skin.

The two main moieties, 3-1-menthoxy propane-1,2-diol and an aromatic aldehyde, of the present invention are widely used as flavor and fragrance components. The present compounds are readily hydrolyzed in the stomach, at approximately pH 2 and are therefore, safe for use.

The present invention is now illustrated in greater detail with reference to the following synthesis examples, examples and comparative examples. However, these synthesis examples, examples and comparative examples are not to be construed to limit the scope of the invention.

The analytical instruments used in the synthesis examples of the present specification were as follows:

(1) Nuclear magnetic resonance spectrum ($^1$H-NMR) :GSX-500 (500 MHz) (manufactured by JEOL)

(2) Mass spectrum (MS):JMS-DX303HF (manufactured by JEOL).

Unless otherwise indicated herein, all parts, percentages, ratios and the like are by weight.

SYNTHESIS EXAMPLE 1

Synthesis of Vanillin-MPD

To a 1.0 liter 2-neck round bottom flask, under a dry nitrogen atmosphere, was added 3,-1-menthoxypropane-1,2-diol (MPD)(17.0 g, 73.9 mmoles), followed by sequential addition of dry toluene (500 ml), vanillin (11.25 g, 73.9 mmoles) and p-toluene sulfonic acid monohydrate (141 mg, 0.74 mmoles).

The flask was equipped with a Dean-Stark apparatus filled with 3A molecular sieves. The mixture was refluxed under a dry nitrogen atmosphere for 42 hours at which time the reaction was determined to be complete by chromatographic analysis.

After cooling to room temperature (about 20° C.–30° C.), the solvent was removed under reduced pressure to obtain a crude oily residue. Purification of the crude oily residue by flash chromatography (silica gel Si-60, ethyl acetate/hexane=1/5 (by volume)) gave pure vanillin-MPD (17.8 g, 48.9 mmoles, 59.4% of theoretical yield).

$^1$H-NMR (500 Mhz, CDCl$_3$, δ ppm): 0.76–0.09 (m, 11 H), 1.25 (m, 1H), 1.35 (m, 1H), 1.62 (m, hZ), 2.1 (m, 1H), 2.2 (m, 1H, 3.1 (m, 1H), 3.3 (m, ½H), 3.4 (m, ½H), 3.54 (m, 1H), 3.66 (m, ½H), 3.75 (m, ½H), 3.85 (m, ½H), 3.91 (s, 3H), 3.96 (m, ½H), 4.08 (m, ½H), 4.25 (m, ½H), 4.35 (m, 1H), 5.66 (s, 1H), 5.73 (s, ½H), 5.8 (s, ½H), 6.91 (m, 1H), 6.99 (m, 2H) MS (m/z): 364 (M+).

SYNTHESIS EXAMPLES 2 to 7

4-(1-Menthoxymethyl)-2-phenyl-1,3-dioxolane or its derivatives as shown in Table 2 below were prepared in the same manner as in Synthesis Example 1 above, except for replacing the substrate, vanillin, with each of the benzaldehyde or its derivatives as shown in Table 2 below.

TABLE 2

| Synthesis Example No. | Substrate | 4-(1-Menthoxy-methyl)-2-phenyl-1,3-dioxolane or its Derivative Produced | Isolated Yield (%) |
|---|---|---|---|
| 2 | Protocatechuic aldehyde | Protocatechuic aldehyde-MPD | 22.0 |
| 3 | Ethyl vanillin | Ethyl vanillin-MPD | 22.0 |
| 4 | Ortho vanillin | Ortho vanillin-MPD | 44.0 |
| 5 | Benzaldehyde | Benzaldehyde-MPD | 63.2 |
| 6 | Anisaldehyde | Anisaldehyde-MPD | 33.5 |
| 7 | Piperonal | Piperonal-MPD | 52.2 |

Spectral data for each is shown below.

Protocatechuic aldehyde-MPD
$^1$H-NMR (500 Mhz, CDCl$_3$, δ ppm): 5.64 (s, ½H, acetal), 5.80 (s, ½H, acetal), 6.55 (br s, 2H, —OH) MS (m/z): 350 (M$^+$)

Ethyl vanillin-MPD
$^1$H-NMR (500 Mhz, CDCl$_3$, δ ppm): 1.44 (t, 3H, —CH$_3$), 4.14 (q, 2H, —OCH$_2$—), 5.72 (s, ½H, acetal), 5.72 (s, 1H, —OH), 5.83 (s, ½H, acetal) MS (m/z): 378 (M$^+$)

Ortho-vanillin-MPD
$^1$H-NMR (500 Mhz, CDCl$_3$, δ ppm): 3.82 (s, 3H, —OCH$_3$), MS (m/z): 364 (M$^+$)

Benzaldehyde-MPD
$^1$H-NMR (500 Mhz, CDCl$_3$, δ ppm): 5.80 (s, ½H, acetal), 5.93 (s, ½H, acetal) MS (m/z): 318 (M$^+$)

Anisaldehyde-MPD
$^1$H-NMR (500 Mhz, CDCl$_3$, δ ppm): 3.82 (s, 3H, —OHC$_3$), 5.76 (s, ½H, acetal), 5.88 (s, ½H, acetal) MS (m/z): 348 (M$^+$)

Piperonal-MPD
$^1$H-NMR (500 Mhz, CDCl$_3$, δ ppm) 5.71 (s, ½H, acetal), 5.96 (s, ½H, acetal), 5.96 (s, 2H, acetal) MS (m/z): 362 (M$^+$)

Example 1

Mouth Sensation of Compounds

Odor evaluation and mouth sensation evaluation were carried out on each compound synthesized in the foregoing Synthesis Examples. The results obtained are shown in Table 3 below.

TABLE 3

| Compound | Characteristic Odor | Mouth Sensation | Longevity of Mouth Sensation | Longevity* of odor on blotting paper |
|---|---|---|---|---|
| Vanillin-MPD | dilute vanilla/odor | hot, tingling, burning, numbing | 3–4 hours | >30 days |
| Protocatechuic aldehyde-MPD | medicinal | hot, pepper, burning | 3–4 hours | — |
| Ethyl vanillin-MPD | vanilla, sweet | oily, metallic | — | >30 days |
| Ortho vanillin-MPD | medicinal, vanilla | bitter, slightly | — | — |

TABLE 3-continued

| Compound | Characteristic Odor | Mouth Sensation | Longevity of Mouth Sensation | Longevity* of odor on blotting paper |
|---|---|---|---|---|
| Benzaldehyde-MPD | sweet, floral | hot bitter | — | >30 days |
| Anisaldehyde-MPD | anisyl odor, sweet | slight sweet, slippery, creamy | 10–15 minutes | >30 days |
| Piperonal-MPD | floral, sweet | bitter | 10 minutes | >30 days |

*Each compound is soaked into a blotting paper and the longevity of the odor is evaluated.

Example 2

Mouth Sensation Enhancement

Compounds of the present invention were tasted pure in small amounts on a wooden toothpick. Thermally hot tea was ingested after a short time.

The temperature of tea was determined subjectively by sipping a cup of tea. In the test, a small amount of vanillin-MPD was applied to the mouth via a wooden toothpick before sipping the tea. In the control, no addition treatment was used.

The compound of the present invention enhanced the thermally hot sensation to cause the tea to taste hotter in comparison with the tea consumed without the compound of this invention.

The results obtained are shown in Table 4 below.

TABLE 4

| | Heat Determination | |
|---|---|---|
| | Within 3 min. | After 30 min. |
| Control | hot | warm |
| Test Compound | very hot | hot |

Example 3

A 1000 ppm ethanol solution of vanillin-MPD was prepared. Using this stock solution, a series of 5 ml samples of vanillin-MPD diluted with water were prepared at 100 ppm, 10 ppm and 1 ppm concentrations.

The procedure used for tasting the samples was as follows. The most dilute sample was tasted first. The sample was gargled for 30 seconds followed by spitting out the solution. Comments were recorded and the next sample was tasted when no effect of the previous sample remained in the mouth.

The results obtained are shown in Table 5 below.

TABLE 5

| Vanillin-MPD | Time | | | |
|---|---|---|---|---|
| | 2–3 min. | 10–15 min. | 30 min. | 120 min. |
| 1 ppm | bitter on sides of tongue, slight tingling, numbing on lips | | | |
| 10 ppm | very bitter, hot sensation on roof of mouth and throat | | | |
| 100 ppm | very hot taste, bitter taste | low level hot, sinus clearing effect, numbing | low level hot, sinus clearing effect, numbing | low level hot, sinus clearing effect, numbing |

Comparative Example 1

Each compound was tasted in the same manner as in Example 3.

The results obtained are shown in Table 6 below. In the table, vanillin-PGA represents propylene glycol acetal of vanillin and vanillin-DEA represents diethyl acetal of vanillin.

TABLE 6

| Compound | Concentration | Characteristics |
|---|---|---|
| Vanillin-MPD | neat | hot, bitter, numbing, lasts over 4 hours |
| Vanillin-PGA | neat | hot bitter taste, lasts only 2–3 minutes |
| Vanillin-DEA | neat | hot bitter taste, lasts only 2–3 minutes |
| Vanillin-DEA | 100 ppm | momentary warm, bitter, sensation is gone in 30 seconds. |

Vanillin-MPD, vanillin-PGA and vanillin-DEA produce hot sensations at slightly different sites in the mouth. Vanillin-MPD is hotter than vanillin-PGA or -DEA.

Example 4

Hard Candy

A hard candy was prepared using 0.0001 to 10% by weight (1 to 100 ppm) of vanillin-MPD as follows:

1 cup of light corn syrup
1 cup of water
2 cups of sugar
¼ teaspoon of flavoring
¼ teaspoon of food coloring
0.0001 or 0.1% by weight of vanillin-MPD The corn syrup, water and sugar were combined in a 2-quart saucepan. The mixture was heated to 300° F. (150° C.) and then removed from the heat. The flavoring, food coloring and vanillin-MPD were then added to the mixture, stirred until blended, poured free-form or into molds and cooled to room temperature to produce a hard candy.

The hard candy thus obtained was tasted and evaluated. The results obtained are shown in Table 7 below.

TABLE 7

| Vanillin-MPD | Time | | | |
|---|---|---|---|---|
| | 2–3 min. | 10–15 min. | 30 min. | 90 min. |
| 1 ppm | slight hot taste, prickly, numbing | slight hot taste, prickly, numbing | | |
| 100 ppm | hot taste, prickly, numbing | hot taste, prickly, numbing, warming sensation spread down to throat | hot taste, prickly, numbing, warming sensation spread down to throat | hot taste, prickly, numbing |

At 100 ppm, vanillin-MPD has a hot taste with a prickly, numbing effect that is mainly on the tongue. It lasts on the tongue for over 90 minutes. This effect spreads throughout the oral cavity. As a result, there is a warming sensation that spreads to the back of the mouth and down the throat. This warming sensation does not last as long as the hot taste, prickly, numbing effects on the tongue.

While the invention has been described in detail and with reference to specific embodiments thereof, it will be apparent to one skilled in the art that various changes and modifications can be made therein without departing from the spirit and scope thereof.

Example 5

Fragrance Composition

A fragrance composition (A) or (B) having the following formulation is prepared.

| Formulation | Parts Per 100 |
|---|---|
| Formulation of fragance composition (A): | |
| Gardenia oil | 45 |
| Vanillin-MPD | 15 |
| rosewood oil | 15 |
| rose oil | 25 |
| Formulation of fragrance composition (B) | |
| Dodecahydro-3a,6,6,9a-tetramethyl-naphtho[2,1-b]furan | 10 |
| Armoise oil | 1 |
| Basil oil | 1 |
| Ciste labdanum sis abs | 1 |
| Citronellol | 5 |
| Cresyl acetate | 0.5 |
| 2,6,6-trimethyl-trans-1-crotonyl-cyclohexene-1 | 5 |
| Eugenol | 1 |
| Galbanum oil 10% | 1 |
| Methyl dihydrojasmonate | 25 |
| 2-acetyl-1,2,3,4,6,7,8-octahydro-2,3,8,8-tetramethylnaphthalene | 20 |
| Lemon oil | 5 |
| 10-oxahexadecanolide | 7 |
| Methyl-2,2,3-cyclopenten-3-yl-1)-5-pentanol-2 | 10 |
| p-isobutyl-α-methyl-dihydrocinnamaldehyde | 5 |
| Vanillin-MPD | 5 |
| Ylang oil extra | 1 |

Vanillin-MPD is preferably formulated into a fragrance composition in an amount of from 0.1% to 30% by weight based on the total weight of the composition.

The fragrance composition comprising 4-(1-menthoxymethyl)-2-phenyl-1,3-dioxolane or a derivative thereof according to the present invention, can further be incorporated into a product, such as a product containing alcohol, preferably in an amount of from 10% to 30% by weight, or in an air freshener product in the form of a solid, a powder, an incense, a gel, a cream, a spray or a liquid, preferably in an amount of from 25% to 55% by weight based on the total weight of the product.

Example 6

Cream

A cream having the following formulation is prepared.

| Cream formulation | Parts |
|---|---|
| Polypropylene stearyl ether (arlamol E) | 20 |
| Vanillin-MPD | 5.0 |
| Stearyl alcohol | 4.0 |
| Steareth 2 (brij 72) | 3.4 |
| Steareth 21 (brij 721) | 1.64 |
| Methyl paraben | 0.02 |
| Water | 65.84 |

Vanillin-MPD is preferably formulated into a cosmetic product, such as a cream, in an amount of from 0.005% to 5% by weight, based on the total weight of the product.

Comparative Example 2

Cream

A cream is prepared in the same manner as in Example 6, except that Vanillin is used in place of Vanillin-MPD.

EVALUATION EXAMPLE 1

Stability of Cream

| | Color | | Odor | |
|---|---|---|---|---|
| Cream | Initial | After 1 week | Initial | After 1 week |
| vanillin (Comp. Ex. 2) | White | Tan, off white | vanilla note | sour note |
| vanillin-MPD (Ex. 6) | White | White | vanilla note | vanilla note |

The enhanced stability of vanillin-MPD to discoloration is illustrated by the above example. Vanillin and vanillin-MPD were added to a standard lotion cream base (both at 5%). After one week at room temperature, the vanillin lotion had discolored to an off-white tan color, while the vanillin-MPD lotion remained unchanged.

EVALUATION EXAMPLE 2

Odor of Cream

| Cream | After 1.5 hour | After 3 hours |
|---|---|---|
| vanillin (Comp. Ex. 2) | vanilla odor | no odor |
| vanillin-MPD (Ex. 6) | vanilla odor | vanilla odor |

Each cream was respectively applied to the back of the hand. The vanillin cream had an immediate off vanilla odor that lasted 1.5 hours. The vanillin-MPD cream had a slight initial vanilla odor, which increased and lasted for 3 hours.

What is claimed is:

1. A fragrance composition comprising a fragrance effective amount of 4-(1-menthoxymethyl)-2-phenyl-1,3-dioxolane or a compound represented by formula (I):

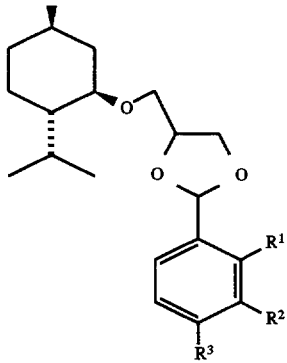

wherein $R^1$ represents a hydrogen atom, a hydroxy group or a lower alkoxy group; $R^2$ and $R^3$, which may be the same or different, each represents a hydrogen atom, a hydroxy group, a lower alkoxy group, or, when taken together, $R^2$ and $R^3$ represents a methylene dioxy group and an acceptable carrier.

2. A fragrance composition comprising 4-(1-menthoxymethyl)-2-phenyl-1,3-dioxolane or a compound thereof represented by formula (I) as in claim 1, wherein $R^1$ is a hydrogen atom, $R^2$ is a methoxy group and $R^3$ is a hydroxy group.

3. A fragrance composition comprising 4-(1-menthoxymethyl)-2-phenyl-1,3-dioxolane or a compound thereof represented by formula (I) as in claim 1, wherein $R^1$ is a hydrogen atom, $R^2$ is a hydroxy group and $R^3$ is a hydroxy group.

4. A fragrance composition as in claim 1, wherein said 4-(1-menthoxymethyl)-2-phenyl-1,3-dioxolane or a compound thereof represented by formula (I) is present in an amount of from 0.0001 to 30% by weight based on the total weight of the composition.

5. A fragrance composition comprising 4-(1-menthoxymethyl)-2-phenyl-1,3-dioxolane or a compound thereof represented by formula (I) as in claim 1, wherein $R^1$ is a hydrogen atom, $R^2$ is an ethoxy group and $R^3$ is a hydroxy group.

6. A fragrance composition comprising 4-(1-menthoxymethyl)-2-phenyl-1,3-dioxolane or a compound thereof represented by formula (I) as in claim 1, wherein $R^1$ is a methoxy group, $R^2$ is a hydroxy group and $R^3$ is a hydrogen atom.

7. A fragrance composition comprising 4-(1-menthoxymethyl)-2-phenyl-1,3-dioxolane or a compound thereof represented by formula (I) as in claim 1, wherein $R^1$ is a hydrogen atom, $R^2$ is a hydrogen atom and $R^3$ is a methoxy group.

* * * * *